United States Patent [19]

Goto et al.

[11] Patent Number: 4,709,383
[45] Date of Patent: Nov. 24, 1987

[54] METHOD FOR EVALUATING RESIDUAL FATIGUE LIFE OF MECHANICAL PARTS

[75] Inventors: Touru Goto; Takashi Konishi, both of Takasago, Japan

[73] Assignee: Mitsubishi Jukogyo Kabushiki Kaisha, Tokyo, Japan

[21] Appl. No.: 868,744

[22] Filed: May 30, 1986

[30] Foreign Application Priority Data

Apr. 21, 1986 [JP] Japan .................................. 61-90025

[51] Int. Cl.$^4$ ............................................. G01N 23/20
[52] U.S. Cl. ...................................... 378/72; 73/808; 378/71
[58] Field of Search ...................... 73/799, 760, 865.8, 73/866, 78, 86, 87, 432.1, 812, 787, 783, 808, 810.1 R; 378/71, 72

[56] References Cited

U.S. PATENT DOCUMENTS

| | | | |
|---|---|---|---|
| 4,287,416 | 9/1981 | Kramer et al. | 378/72 |
| 4,402,227 | 9/1983 | Hayashi et al. | 73/812 |
| 4,404,682 | 9/1983 | Hayashi et al. | 378/72 |
| 4,426,718 | 1/1984 | Hayashi et al. | 378/72 |

Primary Examiner—Michael J. Tokar
Assistant Examiner—Robert R. Raevis
Attorney, Agent, or Firm—Wenderoth, Lind & Ponack

[57] ABSTRACT

A method for evaluating a residual fatigue life of mechanical parts, consisting of the steps of grinding a surface layer of a mechanical part to be inspected by a minute amount to form an inspection surface, measuring half-width data of an X-ray diffraction intensity curve on the inspection surface, calculating a depth (do) of a fatigue damaged region from a graph of a half-width ratio (H/Ho) versus a depth (d) below the surface layer, and determining a fraction of fatigue life N/Nf on the basis of data of the depth (do) of the defective region versus the fraction of fatigue life N/Nf which were separately obtained from a test piece.

5 Claims, 9 Drawing Figures

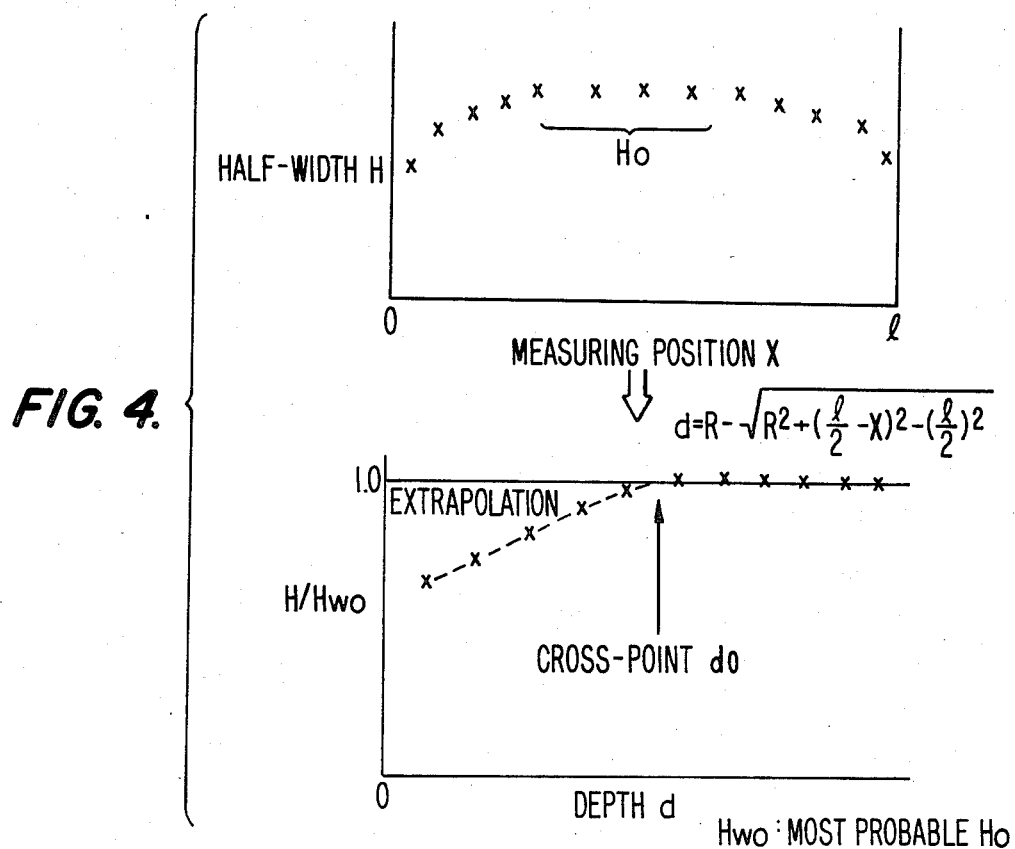
FIG. 4.
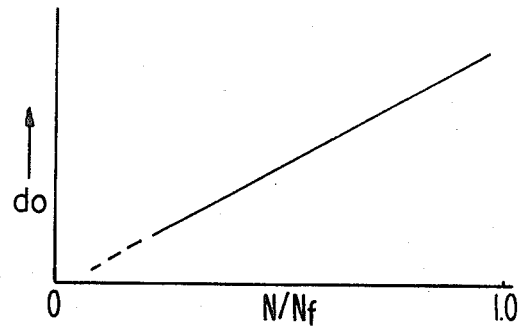
FIG. 5.
FIG. 7.
(PRIOR ART)
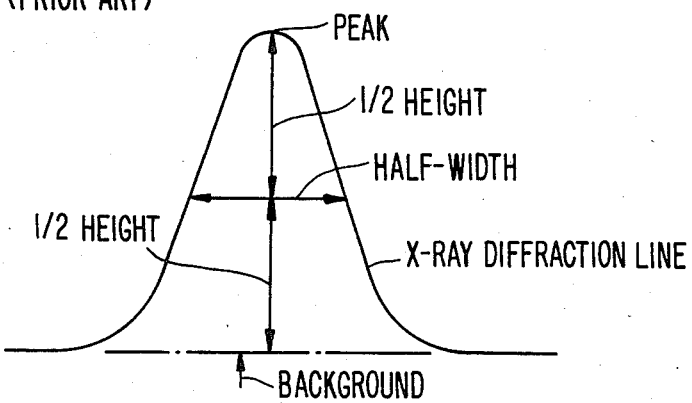

SOFT MATERIAL

HARD MATERIAL

METHOD FOR EVALUATING RESIDUAL FATIGUE LIFE OF MECHANICAL PARTS

BACKGROUND OF THE INVENTION

1. Field of the Invention.

The present invention relates to improvements in a method for evaluating residual fatigue life of mechanical parts.

2. Description of the Prior Art.

Heretofore, in a process of maintenance and control for mechanical parts a crack finding inspection was carried out, but according to this inspection it was only possible to determine whether the parts have reached their useful life or not. As methods for estimating approximately when cracks will be generated from a result of an inspection conducted prior to generation of cracks, there can be conceived a method of detecting changes in the nature of material at the surface of mechanical parts prior to generation of cracks and a method of observing micro cracks, but either of these methods is poor in precision, and there has been almost no example of success as a practical method.

As a representative one of the methods for detecting changes in the nature of material, there is a method of making use of the X-ray diffraction process and paying attention to changes in a profile of the X-rays diffracted from a part. A description will now be made outlining this method with reference to FIG. 7.

FIG. 7 is a schematic diagram showing a general X-ray diffraction intensity curve, and a half-width indicated in this figure means a width of a peak at a ½ height of the peak in a profile of the diffracted X-rays. Representing the half-width by H and that before use of the part by Ho, then as shown, for example, in FIGS. 8(a) and (b), a halfwidth ratio H/Ho at the surface of a test sample has a good correlation to a fatigue damage ratio N/Nf (N: number of repetitions of stress, Nf: number of repetitions of stress at fracture). Accordingly, a degree of fraction of fatigue life can be estimated from a half-width ratio.

However, as it is seen in FIGS. 8(a) and (b), although change of a half-width H/Ho occurs remarkably in the first period I, the gradient of change of H/Ho with respect to a fraction of fatigue life N/Nf in the second period II which occupies most of the fatigue life is small. Therefore, precision in prediction of the fatigue life is poor. Also, in general cases, the initial value of Ho is not knwon for the mechanical parts except if Ho was measured before service. Therefore, Ho should be estimated by any method, though the reliability of predicted fatigue life depends strongly on the accuracy of the estimated Ho.

These two reasons have made the method utilizing X-ray diffraction measurement at the surface of mechanical parts unsuccessful. The third period III in FIGS. 8(a) and (b) involves the process of generation and propagation of macroscopic cracks, and this period is outside of the object of inspection according to the present invention.

SUMMARY OF THE INVENTION

It is therefore one object of the present invention to provide an improved method for evaluating the residual fatigue life of mechanical parts making use of the X-ray diffraction process, which is free from the shortcomings of a similar method in the prior art.

A more specific object of the present invention is to provide a method for evaluating the residual fatigue life of mechanical parts, which has a high precision even in the second period of a fatigue life.

According to one feature of the present invention, there is provided a method for evaluating the residual fatigue life of mechanical parts, consisting of the steps of grinding a surface layer of a mechanical part to be inspected by a minute amount to form an inspection surface, measuring half-width data of an X-ray diffraction intensity curve on an inspection surface, measuring a fatigue damaged depth do where the half-width H is different from the initial value Ho by plotting half-width versus a depth d from the inspection surface, and determining an amount of fatigue damage on the basis of data of the fatigue damaged depth do versus a fraction of fatigue life N/Nf which were separately obtained from test pieces.

In the second period II, while changes in the nature of the material are relatively stabilized on the surface, the changes in the nature of the material proceed towards the interior of the material during this second period II, and therefore, according to the present invention, since a depth of a surface layer in which changes in the nature of material have occurred is measured and used as a parameter for evaluating the residual fatigue life, precision in the evaluation of the residual fatigue life can be enhanced. As previously mentioned, in any X-ray methods for fatigue damage detection, the initial value Ho of the half-width H is necessary. However, the initial value Ho is not known from general inspections, as such, a half-width value measured at a location where a loaded stress is estimated to be small and the material is subjected to almost no fatigue damage, is substituted therefor. However, in a mechanical structure, since the nature of the material is already not uniform at the time of manufacture, a location where the material is not subjected to fatigue damage which is as close as possible to the location whose fatigue damage is inspected, can only give the most probable initial value Ho.

The calculation of the most probable initial value Hwo is possible utilizing the present invention. According to another feature of the present invention, there is provided a method for evaluating residual fatigue life of mechanical parts on the basis of observation of microscopic cracks at the very surface in the proximity of both ends of the inspection surface.

In the second period II where the change of H/Ho is stabilized, nuclei of cracks are developing. Furthermore, towards the end of the second period II, microscopic cracks should appear. Therefore, the observation of microscopic cracks will also assure the reliability of fatigue damage inspection.

SUMMARY OF THE INVENTION

An object of the present invention is to make measurements of the profile of diffracted X-rays at the successive points on an inspection surface that is horizontally ground by a minute amount, and plotting these values as shown in FIG. 3. If the ground depth is sufficient, the non-damaged region will appear around the center of the inspection surface having a length l, and the plotting of H versus x, the distance at a point measured from one end of the inspection surface as shown in FIG. 3, should have a flat portion at around an x of one-half of l. The value of H at the flat portion yields the most probable value of Ho. In order to represent a depth d from a surface at the successive measuring positions x, geometrically d can be calculated from the following equation:

$$d = R - \sqrt{R^2 + \left(\frac{l}{2} - x\right)^2 - \left(\frac{l}{2}\right)^2}$$

Where R is radius of a mechanical part, l is the length of inspection surface and x is the distance from the end of the inspection surface. Then, the plotting of H/Ho versus d can be easily calculated as explained in FIG. 4. From a cross-point between two lines in the lower graph of FIG. 4, a depth do of a fatigue damaged region can be determined. Hence, the amount of fatigue damage and the residual life can be determined utilizing the calibration curve of do versus a fraction of fatigue life N/Nf that is separately obtained with respect to a test piece as shown in FIG. 5.

BRIEF DESCRIPTION OF THE DRAWINGS

In the accompanying drawings.

FIG. 4 is a diagram prepared by rearranging the data in FIG. 3 into the form of a half-width ratio (H/Ho) versus a depth (d) from a surface;

FIG. 5 is a calibration diagram of a depth (do) of a fatigue damaged region versus fraction of fatigue life N/Nf;

FIG. 7 is a diagram to be used for explaining a half-width of an X-ray diffraction intensity curve.

DESCRIPTION OF THE PREFERRED EMBODIMENT

Figure 1:
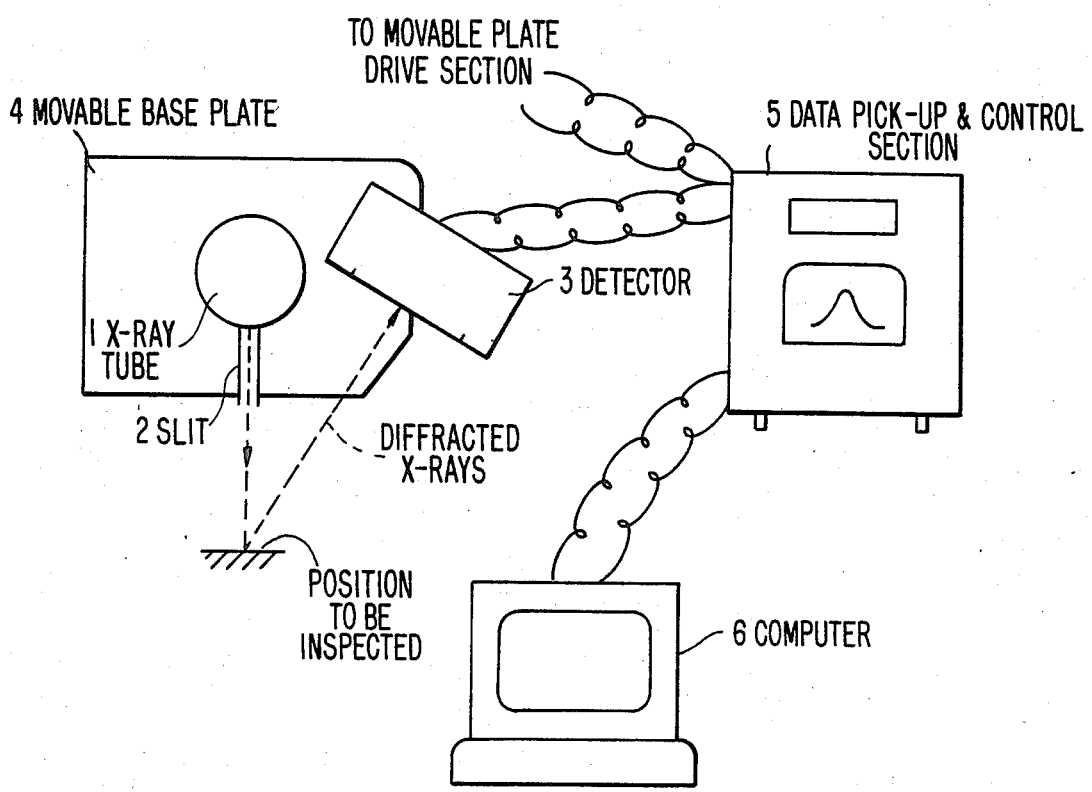
FIG. 1 is a schematic illustration of an X-ray diffraction system to be used for practicing the method for evaluating the residual fatigue life of mechanical parts according to the present invention.

Now one preferred embodiment of the present invention will be explained with reference to FIGS. 1 through 7.

An inspection surface is formed by removing, such as by grinding, a surface layer of a mechanical part to be inspected by a minute amount. For this formation of an inspection surface, for example, the means disclosed in copending Japanese Patent Application No. 60-53796 (See FIG. 6) could be employed. For example, the material 11 to be inspected is clamped to a table by means of a holding band 16 and supports 15. A grinding tool 14 is mounted on a base plate 19 extending from a movable truck 13 which slides along a linear rail 12 on the table. The grinding tool 14 removes hard scale 17 on the material 11 and cuts through a surface layer 18 on the material 11 to form the inspection surface.

Figure 3:
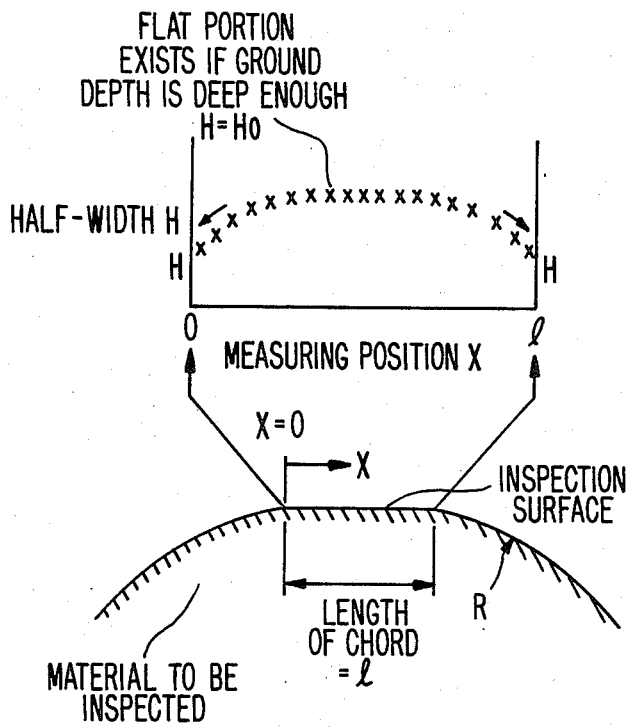
FIG. 3 is a diagrammatic representation of data picked up according to the method of the present invention.

From the measurements of an X-ray diffraction intensity curve on the above-referred inspection surface (See FIG. 7), data (a half-width H versus a measuring position x) as shown in FIG. 3 are picked up. In FIG. 3, in the case where a flat portion appears at the position corresponding to the center of a chord formed by grinding a curved surface of a member, the half-width H at the flat portion is employed as a half-width Ho of unused material. The half-width H obtained at the flat portion is the most probable original half-width Ho. Upon picking up these data, for example, the means disclosed in copending Japanese Patent Application No. 60-53797 could be employed.

The respective measuring positions are represented in terms of horizontal coordinate x (See FIG. 3), R represents a radius of a circular member to be inspected, l represents a length of the chord formed as an inspection surface, whereby the horizontal coordinate x can be transformed into a depth d from a surface by the following formula:

$$d = R - \sqrt{R^2 + \left(\frac{l}{2} - x\right)^2 - \left(\frac{l}{2}\right)^2}$$

Then, the half-width ratio H/Ho can be plotted as a function of the depth d. This is shown in FIG. 4.

These plotted data align, in general, on two intersecting straight lines. More particularly, at the positions of deep depth d, the data align on a flat horizontal line, and in a damaged region where the depth d is smaller, the data points deviate linearly, in general, from the level of the flat straight line. Therefore, the cross-point between these two imaginary straight lines are sought by statistically analyzing the data, and from the horizontal coordinate of the cross-point, a depth do of the defective region is determined.

The relation between the depth do and a fraction of fatigue life N/Nf is separately measured by means of a test piece, and the fraction of fatigue life N/Nf is determined on a diagram of do versus N/Nf, which is shown in FIG. 5.

Figure 8A:
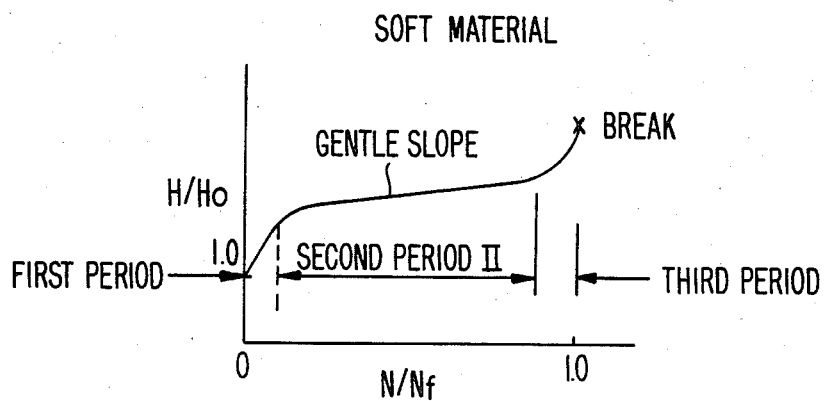
FIG. 8 shows determination curves in the prior art used for estimating a degree of fatigue damage from changes of a half-width at the surface of mechanical parts, FIG. 8(a) showing the variation of half-width due to fatigue of soft material and FIG. 8(b) showing the variation of half-width due to the fatigue of hard material.
Figure 8B:
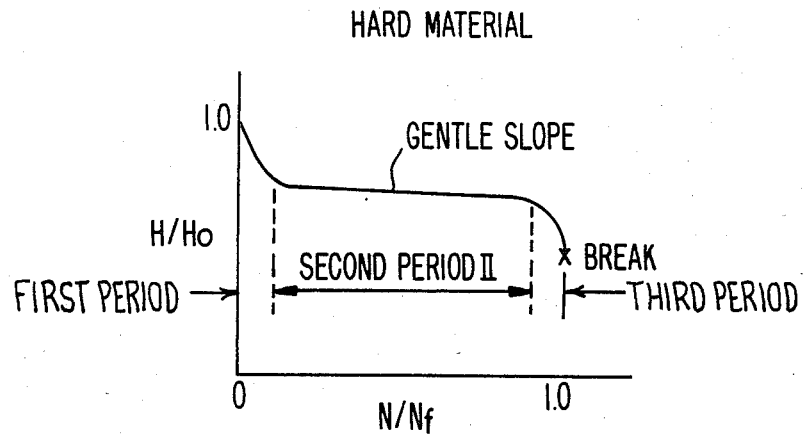

When N/Nf is close to 1.0, the possibility that microscopic cracks may be generated is large. Therefore, determination of the amount of fatigue damage estimated by the method relying upon X-ray diffraction can be done by carrying out observation of the inspection surface at the very surface in the proximity of the both ends of the prepared inspection surface. In addition at around the upper limit of fatigue life, changes in the half-width ratio (H/Ho) (H represents a half-width at the surface obtained by extrapolation as shown in FIG. 4) becomes large. Therefore, the confirmation can be done also through the method in the prior art illustrated in FIG. 8.

It is to be noted that microscopic cracks are present within a very shallow surface layer. Therefore, although the observation of a practically operating mechanical part to which scale has adhered as a result of use was impossible, in the method of forming an inspection surface according to the above-referred copending Japanese Patent Application No. 60-53796, the surface layer is cut away obliquely so as to be exposed, and so, the observation becomes easy.

Figure 6:
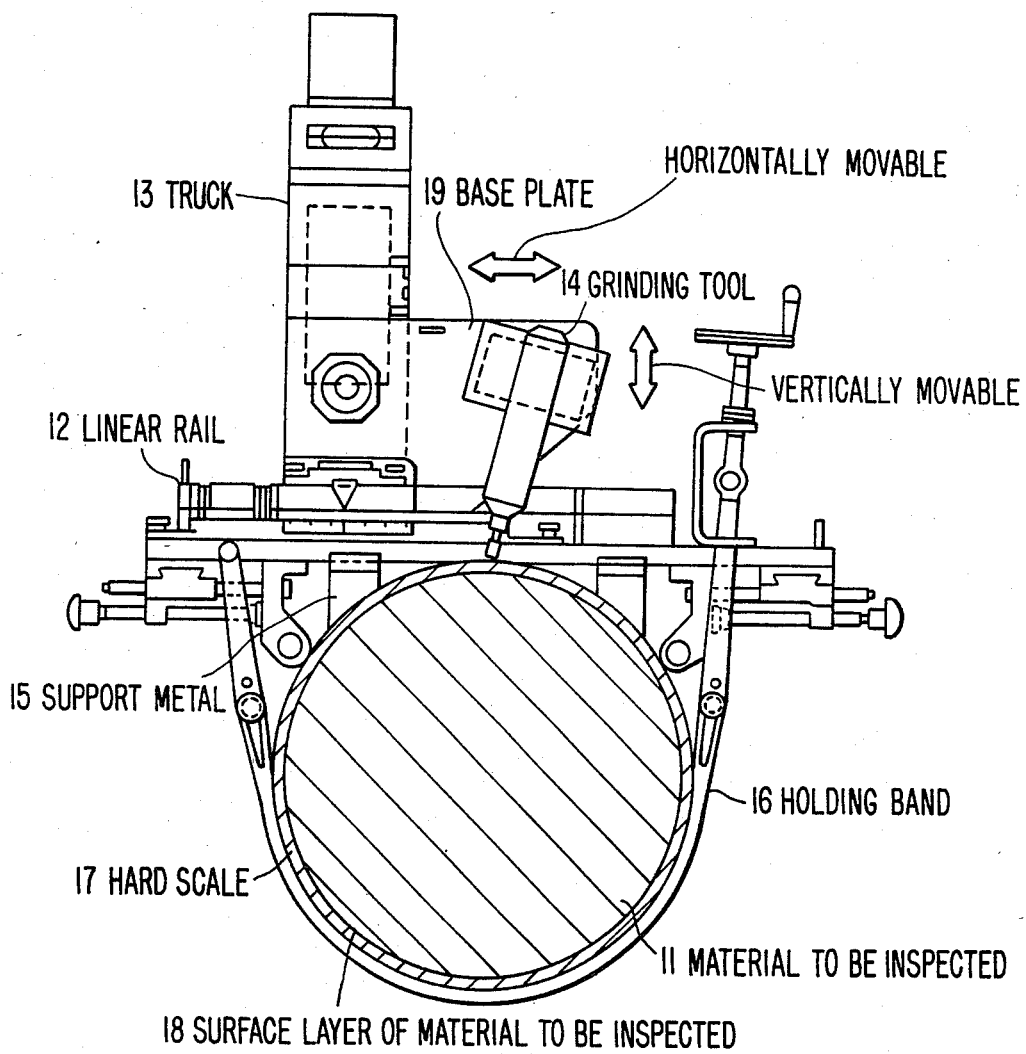
FIG. 6 is a schematic view of an apparatus for forming an inspection surface.

Now, description will be made on an X-ray diffraction apparatus shown in FIG. 1. The diffraction apparatus is composed of an X-ray tube 1, a slit 2 and a detector 3, and these component parts are disposed on a movable base plate 4 that is part of an inspection surface forming apparatus (FIG. 6). A detection signal issued from the detector 3 is sent through a data pick-up and control section 5 to a computer 6, and control signals issued from the computer 6 are transmitted via the data pick-up and control section 5 to a drive section for the movable base plate 4 and the detector 3. The apparatus operates according to the flow chart shown in FIG. 2 as follows:

(1) Under control of the computer 6, each time the X-ray diffraction apparatus has picked up an X-ray diffraction curve for a given position at a distance x, the movable base plate 4 is automatically advanced in a stepwise manner. Each time, the distance x and the corresponding half-width H of the X-ray diffraction curve are calculated and recorded.

(2) A diagram of the half-width ratio versus the depth d is produced by the computer 6, and then it is determined whether or not a highly probable original half-width Ho has been obtained, that is, whether the depth ground on the sample is deep enough to produce a half-wdith Ho at a portion of the material which has not undergone fatigue damage. If the probability is not sufficient, the inspection surface is ground again to obtain a larger crosssection chord length l.

(3) Then, the depth do of the fatigue damaged region is read out from the diagram of H/Ho versus d.

(4) On the basis of this value of the depth do, the fraction of fatigue life N/Nf is determined. If the amount of N/Nf is close enough to 1.0, an instruction for observation of microscopic cracks at the both ends of the inspection surface is issued.

(5) As a result of the observation of microscopic cracks, that is, if microscopic cracks are observed by an operator or suitable equipment, an instruction is issued from the computer 6 that any disposal of the parts inspected should be done in the near future.

(6) If microscopic cracks are not present, an instruction is issued from the computer 6 that reinspection should be carried out in the near future.

(7) In the event that the amount of N/Nf is small and thus significant fatigue life of the part being tested remains, on the basis of the value obtained by subtraction of 1−N/Nf, the timing of when the next inspection should be carried out during the remaining useful life of the part, is determined.

Figure 2:
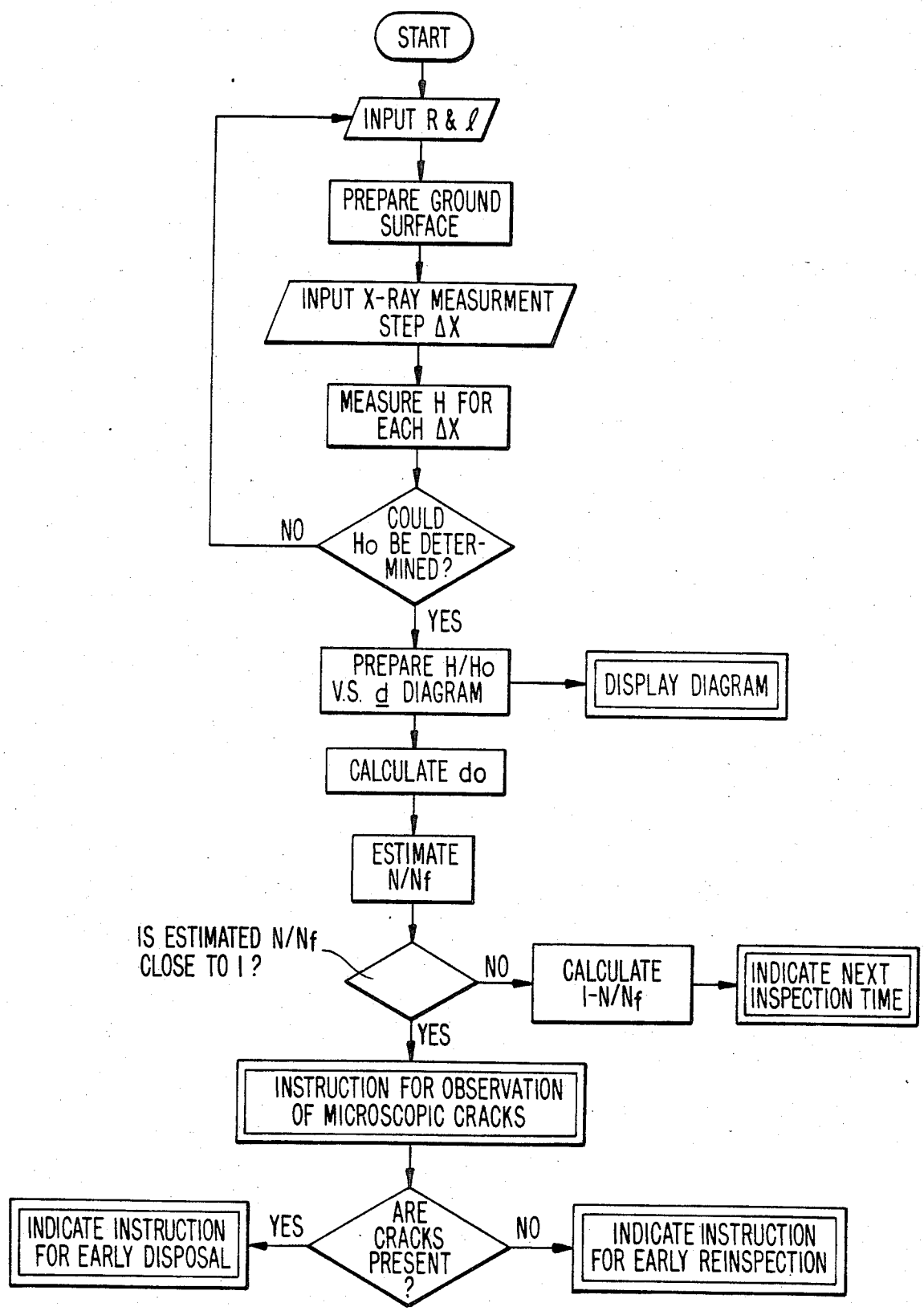
FIG. 2 is a flow chart of the inspection and a computer program used in the system shown in FIG. 1.

The operation steps (1) to (7) above are programmed with software used with the computer 6. That is, the operation of the computer 6 is represented in a flow chart as shown in FIG. 2.

Since the present invention is characterized by the above-described feature, the following advantages can be obtained.

(1) Due to the fact that upon determining an amount of fatigue damage, the depth of a surface layer in which changes of nature of material have occurred is measured and it is used as a parameter for evaluating the remaining useful life of the part, precision in evaluation of the residual life can be enhanced.

(2) In addition, precision in evaluation of the residual life can be enhanced by employing a half-width value measured at a location not subjected to fatigue damage but which is as close as possible to the location being evaluated, as an initial half-width value Ho.

Although certain preferred embodiments have been shown and described, it should be understood that many changes and modifications may be made therein without departing from the scope of the appended claims.

What is claimed is:

1. A method for evaluating a residual fatigue life of mechanical parts characterized by the steps of grinding a minute amount of a surface layer of a mechanical part to be inspected to form an inspection surface, measuring half-width data of an X-ray diffraction intensity curve at points corresponding to various depths below the surface layer along said inspection surface and determining a depth (do) below the surface layer of a fatigue damaged region of the mechanical part inspected from a graph of a half-width ratio (H/Ho) versus a depth (d) below the surface layer where H is the measured half-width of the X-ray diffraction intensity curve and Ho is the half-width of the X-ray diffraction intensity curve at a depth below the surface layer of the mechanical part which has not been damaged by fatigue, and determining a fraction of fatigue life N/Nf on the basis of data of said depth (do) of the fatigue damaged region versus the fraction of fatigue life N/Nf which were separately obtained from a test piece.

2. A method for evaluating a residual fatigue life of mechanical parts characterized by the steps of grinding a minute amount of a surface layer of a mechanical part to be inspected to form an inspection surface, measuring half-width data of an X-ray diffraction intensity curve at points corresponding to various depths below the surface layer along said inspection surface and determining a depth (do) of a fatigue damaged region from a graph of a half-width ratio (H/Ho) versus a depth (d) below the surface layer where H is the measured half-width of the X-ray diffraction intensity curve and Ho is the half-width of the X-ray diffraction intensity curve at a depth below the surface layer of the mechanical part which has not been damaged by fatigue, and determining the fraction of fatigue life N/Nf on the basis of data of said depth (do) of the fatigue damaged region versus the fraction of fatigue life N/Nf which were separately obtained from a test piece, as well as on the basis of observation of microscopic cracks at the very surface in the proximity of both ends of said inspection surface.

3. A method for evaluating residual fatigue life of a mechanical part comprising:

performing a fatigue test on a test piece and determining a graph of a first do as a function of a fraction of fatigue life N/Nf of the part, where do is the depth of a fatigue damaged region, Nf is the number of repetitions of stress at fracture of the part and N is the number of repetitions of stress the part is subjected to;

removing a surface layer of the mechanical part which has been in use and is to be inspected such that an inspection surface is formed on the mechanical part with each of a plurality of points along the inspection surface corresponding to a depth d below the original surface layer;

measuring half-width data of an X-ray diffraction intensity curve at said points along said inspection surface, and determining a depth of a second do corresponding to a depth of a fatigue damaged region of the mechanical part from a graph of a half-width ratio H/Ho versus d where H is the measured half-width of the X-ray diffraction intensity curve, Ho is the half-width of the X-ray diffraction intensity curve at a depth which has not been damaged by fatigue below the original surface layer of the mechanical part; and comparing the value of the second do of the mechanical part with the previously determined first do versus N/Nf graph measured for the test piece which has not been put into use to thereby determine the remaining fraction of fatigue life (1-N/Nf) of the mechanical part.

4. The method for evaluating residual fatigue life of mechanical parts of claim 3, further comprising determining whether the estimated N/Nf is close to 1.0 and if the N/Nf is close to 1.0, examining regions of the inspection surface close to the original surface layer to determine the presence of microscopic cracks thereat.

5. The method for evaluating residual fatigue life of mechanical parts of claim 3, wherein Ho is determined by measuring the half-width of the X-ray diffraction intensity curve at a point along the inspection surface corresponding to a depth at which the part has not been damaged by fatigue.

* * * * *